United States Patent

Bitowft et al.

[11] Patent Number: 6,060,637
[45] Date of Patent: *May 9, 2000

[54] SHIELD FOR ABSORBENT PRODUCTS

[75] Inventors: Bruce Kevin Bitowft, Glashutten; Karsten Puchert, Griesheim, both of Germany; Michael Edward Carrier, Cincinnati, Ohio; Ralf Geilich, Crailsheim, Germany

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,420
[22] PCT Filed: May 12, 1995
[86] PCT No.: PCT/US95/05904
  § 371 Date: Feb. 28, 1997
  § 102(e) Date: Feb. 28, 1997
[87] PCT Pub. No.: WO95/31167
  PCT Pub. Date: Nov. 23, 1995

[30] Foreign Application Priority Data

May 13, 1994 [EP] European Pat. Off. ............. 94107422

[51] Int. Cl.[7] ..................................... A61F 13/15
[52] U.S. Cl. .......................... 604/368; 604/378; 604/383
[58] Field of Search ................... 604/378, 368, 604/385.1, 366, 372, 383, 384

[56] References Cited

U.S. PATENT DOCUMENTS

| 4,321,924 | 3/1982 | Ahr | 604/385.1 |
|---|---|---|---|
| 4,626,254 | 12/1986 | Widlund et al. | 604/383 |
| 4,752,349 | 6/1988 | Gebel | 604/370 |
| 4,762,521 | 8/1988 | Roessler et al. | 604/378 |
| 5,009,653 | 4/1991 | Osborn, III | 604/385.1 |
| 5,175,046 | 12/1992 | Nguyen | 428/198 |
| 5,188,624 | 2/1993 | Young, Sr. et al. | 604/378 |
| 5,356,403 | 10/1994 | Faulks et al. | 604/378 |
| 5,437,653 | 8/1995 | Gilman et al. | 604/378 |
| 5,458,592 | 10/1995 | Abuto et al. | 604/378 |
| 5,460,623 | 10/1995 | Emenaker et al. | 604/368 |
| 5,509,914 | 4/1996 | Osborn, III | 604/368 |
| 5,533,991 | 7/1996 | Kirby et al. | 604/383 |
| 5,591,149 | 1/1997 | Cree et al. | 604/378 |
| 5,643,240 | 7/1997 | Jackson et al. | 604/378 |
| 5,827,255 | 10/1998 | Crainic | 604/378 |

Primary Examiner—John G. Weiss
Assistant Examiner—Dennis Ruhl
Attorney, Agent, or Firm—Jeffrey V. Bamber; Matthew P. Fitzpatrick

[57] ABSTRACT

The invention relates to absorbent products (1) like baby diapers, adult incontinence products and particularly to sanitary napkins or pantyliners. These absorbent products all have absorbent cores (4) which according to the present invention comprise absorbent gelling materials (5) in granular form or other particles. A problem associated with such cores is that these particles can migrate out of the article along the paths of liquid entry into the product. Therefore, a shield (8) positively separating the paths of liquid transport into the product from the particles is provided for absorbent structures according to the invention.

1 Claim, 2 Drawing Sheets

SHIELD FOR ABSORBENT PRODUCTS

FIELD OF THE INVENTION

The present invention relates to absorbent products like baby diapers, adult incontinence products and particularly to sanitary napkins or pantyliners. These absorbent products all have absorbent cores which according to the present invention comprise absorbent gelling materials in granular form or other particles. A problem associated with such cores is that these particles can migrate out of the article along the paths of liquid entry into the product and then become recognisable to the user while also being lost for the absorptive capacity of the article. Therefore a shield positively separating the paths of liquid transport into the product from the particles is provided for absorbent structures according to the invention.

BACKGROUND OF THE INVENTION

The problem of migrating particles of highly absorbent material has been considered in several publications but to the knowledge of the inventors it has not yet been satisfactorily resolved. For example U.S. Pat. No. 4,321,924 discloses a sanitary napkin which comprises a fibrous layer as part of the topsheet to improve strike through characteristics of the absorbent article. However no disclosure of the appropriate size of pores in the topsheet is given and the problem of particle migration in absorbent structures is not touched upon.

U.S. Pat. No. 4,752,349 discloses a sanitary napkin wherein a wicking layer adjacent to the topsheet extends beyond the periphery of the absorbent core. It therefore would serve as a barrier along a straight line between particles in said absorbent core and the liquid passage ways in the topsheet of the sanitary napkin. However no barrier against migration around the edge of the tissue is foreseen or considered since this disclosure does not relate to the same problem underlying the present invention.

U.S. Pat. No. 5,009,653 shows absorbent gel material containment structures interposed between topsheet and backsheet of absorbent articles. This patent addresses the problem of particle migration from the absorbent structure through the liquid passage ways in the topsheet and implies that a wetlaid tissue between the topsheet and the absorbent structure would reduce absorbent gel material particles migration. However as in the above cited prior art no shielding at the edge of the wetlaid tissue is provided for.

EP-A-248 584 also discloses sanitary napkins which have fully enclosed absorbent structures by providing several layers of tissue around the particle containing absorbent structure. However these tissues are not joined to each other along an endless peripheral line such that particle migration paths remain open for particles to ultimately migrate through the liquid passage ways in the topsheets employed in these articles.

It is therefore an objective of the present invention to fully shield absorbent structures comprising absorbent particles from the liquid passage ways in the topsheet of absorbent articles. In particular tissues having pore sizes smaller than the smallest particle are desirable since they simultaneously perform as wicking and distribution layers while serving as particle migration shields.

BRIEF DESCRIPTION OF THE INVENTION

The present invention relates to an absorbent product comprising a topsheet with liquid passage ways, a liquid impervious backsheet and an absorbent core enveloped between the topsheet and the backsheet. The core comprises dry absorbent particles or other particles which are capable of permeating in their dry state through the topsheet along the liquid passage ways. The absorbent product further comprises a permeation blockage means to restrict permeation of the particles to the liquid passage ways of the topsheet. The permeation blockage means is placed between the topsheet and the absorbent core and is joined to the backsheet, topsheet or both such that it is shielding the particles from the liquid passage ways.

Preferably the permeation blockage means is a nonwoven substrate with a maximum pore size of less than 60 micro meters. In a preferred embodiment the permeation blockage means extends beyond the core and is attached to the backsheet while it can or can not extend to the full size of the backsheet itself.

The permeation blockage means can also be joined to the topsheet such that all liquid passage ways are encircled by the line of joining between said permeation blockage means and the topsheet such that the objective of shielding the particles from the liquid passage ways is achieved.

Finally in a particularly preferred embodiment the permeation blockage means extends beyond the perimeter of the core of the absorbent article and is joined simultaneously to the topsheet and the backsheet of the absorbent article most preferably along a single endless line which simultaneously forms the peripheral edge of the absorbent product itself. In this embodiment, however, the joining has to be such that wicking through the side seal of the absorbent product is prevented or alternatively the permeation blockage means does not support liquid transport within its own plane.

Definitions

As used herein, the term "aqueous body fluids" includes urine, menses and vaginal discharges.

As used herein, the term "absorbent product" refers to articles which are capable of absorbing aqueous body fluids like disposable baby, children or adult diapers, incontinence products like inserts or bed pads and sanitary napkins.

As used herein, the term "sanitary napkin" refers to an absorbent article that is worn by females adjacent to the pudendal region, generally external to the urogenital region, and which is intended to absorb and contain aqueous body fluids and other vaginal discharges from the wearer's body. It should be understood, however, that the present invention is also applicable to other feminine hygiene or catamenial pads such as pantyliners, or other absorbent articles such as incontinence pads, and the like.

All percentages, ratios and proportions used herein are by weight unless otherwise specified.

DETAILED DESCRIPTION OF THE INVENTION

Figure 1:
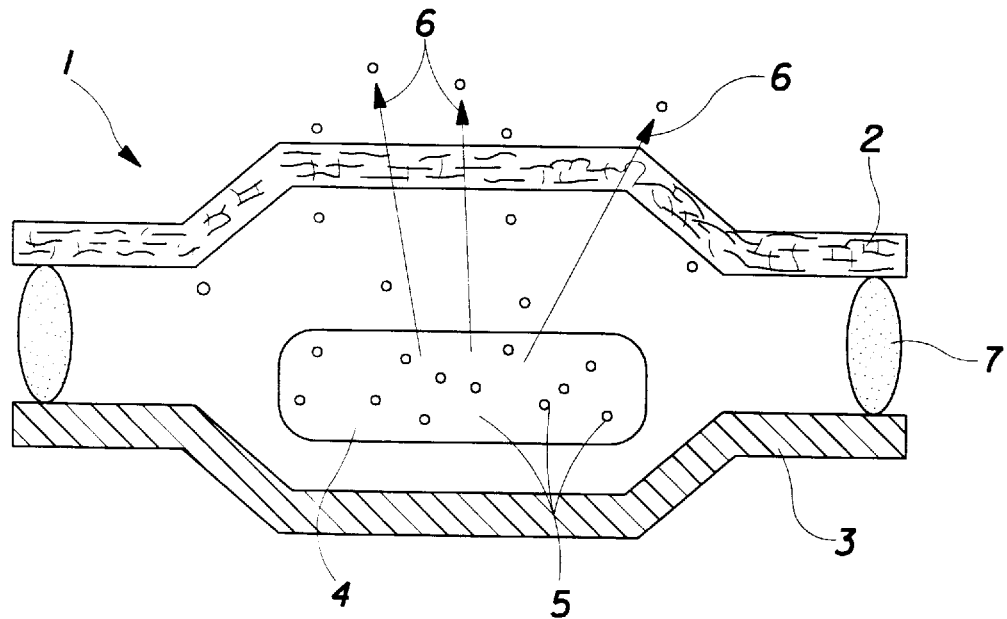
FIG. 1 in a cross sectional view of a prior art absorbent structure construction without barrier or shield against particle migration losses.

According to the present invention the absorbent product comprises three main elements: a topsheet, a core and a backsheet. Typically the topsheet is worn next to the skin of the user while the backsheet is worn next to the undergarment of the user with the core enveloped between both. This structure as known from the prior art is principally shown in FIG. 1 where a liquid permeable topsheet (2) overlays a core (4), which comprises particles (5). The backsheet (3) is joined to the topsheet (2) by joining means (7), preferably by crimping seals or adhesive seals. The particles (5) are capable of permeating in their dry state through the topsheet (2) as indicated by arrows (6) in the prior art embodiment of FIG. 1. Each of the three main elements of the absorbent product can be selected from a wide variety of alternatives and can also comprise several elements contributing to the individual function of each of the main elements.

According to the invention the absorbent product further comprises a permeation blockage means (8) which is joined to either the backsheet (3), the topsheet (2) or both in order to shield the particles (5) form the liquid passage ways in the topsheet (2). This can be achieved for example by an endless line of attachment (9) shown in FIGS. 2, 3, 4 which can be separate from the joining means (7).

In the following non-limiting embodiments of the main elements of the absorbent product are described.

Absorbent core

This absorbent core is shown as a single entity (4) in all Figures. It typically includes the following components: (a) optionally a primary fluid distribution layer; (b) optionally, but preferably, a secondary fluid distribution layer; (c) a fluid storage layer, (d) optionally a fibrous ("dusting") layer underlying the storage layer; and (e) other optional components.

a. Primary Fluid Distribution Layer

One optional component of the absorbent cores according to the present invention is the primary fluid distribution layer. This primary distribution layer typically underlies the topsheet and is in fluid communication therewith. The topsheet transfers the acquired menstrual fluid to this primary distribution layer for ultimate distribution to the storage layer. This transfer of fluid through the primary distribution layer occurs not only in the thickness, but also along the length and width directions of the absorbent product.

b. Optional Secondary Fluid Distribution Layer

Also optional but preferred component of the absorbent cores according to the present invention is a secondary fluid distribution layer. This secondary distribution layer typically underlies the primary distribution layer and is in fluid communication therewith. The purpose of this secondary distribution layer is to readily acquire menstrual fluid from the primary distribution layer and transfer it rapidly to the underlying storage layer. This helps the fluid capacity of the underlying storage layer to be fully utilized.

c. Fluid Storage Layer

Positioned in fluid communication with, and typically underlying the primary or secondary distribution layers, is a fluid storage layer comprising certain absorbent gelling materials usually referred to as "hydrogels," "superabsorbent" "hydrocolloid" materials. Absorbent gelling materials are those materials that, upon contact with aqueous fluids, especially aqueous body fluids, imbibes such fluids and thus form hydrogels. These absorbent gelling materials are typically capable of absorbing large quantities of aqueous body fluids, and are further capable of retaining such absorbed fluids under moderate pressures. These absorbent gelling materials are also typically in the form of discrete, nonfibrous particles.

This fluid storage layer can comprise solely absorbent gelling materials, or these absorbent gelling materials can be dispersed homogeneously or non-homogeneously in a suitable carrier. Suitable carriers include cellulose fibers, in the form of fluff, such as is conventionally utilized in absorbent cores. Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferred synthetic fibers have a denier of from about 3 denier per filament to about 25 denier per filament, more preferably from about 5 denier per filament to about 16 denier per filament. Also preferably, the fiber surfaces are hydrophilic or are treated to be hydrophilic. The storage layer can also include filler materials, such as Perlite, diatomaceous earth, Vermiculite, etc., that lower rewet problems.

If dispersed non-homogeneously in a carrier, the storage layer can be locally homogeneous, i.e. have a distribution gradient in one or several directions within the dimensions of the storage layer. Non-homogeneous distribution can also refer to laminates of carriers enclosing absorbent gelling materials partially or fully (i.e. with or without migration possibilities).

Generally, the storage layer comprises from about 15 to 100% absorbent gelling materials and from 0 to about 85% carrier. Preferably, the storage layer comprises from about 30 to 100%, most preferably from about 60 to 100% absorbent gelling materials and from 0 to about 70%, most preferably from 0 to about 40%, carrier.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose. Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and crosslinking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al), issued Feb. 28, 1978. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole percent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

While these absorbent gelling materials are typically in particle form, it is also contemplated that the absorbent gelling material can be in the form of macrostructures such as fibers, sheets or strips. These macrostructures are typically prepared by forming the particulate absorbent gelling material into an aggregate. treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992.

d. Optional Fibrous ("Dusting") Layer

An optional component for inclusion in the absorbent cores according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macrostructures such as fibers, sheets or strips, this fibrous "dusting" layer need not be included. However, because this "dusting" layer provides some additional fluid-handling capabilities such as rapid wicking of fluid along the length of the pad, its inclusion is typically preferred in absorbent cores according to the present invention.

e. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention.

Another component which can be included in the absorbent core according to the invention and preferably is provided close to or as part of the primary or secondary fluid distribution layer are odor control agents. Typically active carbon coated with or in addition to other odor control agents, in particular suitable zeolite or clay materials, are optionally incorporated in the absorbent core. These components can be incorporated in any desired form but often are included as discrete, non-fibrous particles.

Topsheet

The topsheet (2) is compliant, soft feeling, and non-irritating to the wearer's skin. The topsheet also can have elastic characteristics allowing it to stretch in one or two directions. Further, the topsheet is fluid pervious permitting fluids (e.g., menses and/or urine) to readily penetrate through its thickness. A suitable topsheet can be manufactured from a wide range of materials such as woven and nonwoven materials, polymeric materials such as apertured formed thermoplastic films, apertured plastic films, and hydroformed thermoplastic films, porous foams; reticulated foams, reticulated thermoplastic films, and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975, U.S. Pat. No. 4,324,246 (Mullane, et al.), issued Apr. 13, 1982, U.S. Pat. No. 4,342,314 (Radel, et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Particularly preferred microapetured formed film topsheets are disclosed in U.S. Pat. No. 4,609,518 (Curro et al), issue Sep. 2, 1986 and U.S. Pat. No. 4,629,643 (Curro et al), issued Dec. 16, 1986. The preferred topsheet for the present invention is the formed film described in one or more of the above patents and marketed on sanitary napkins by The Procter & Gamble Company of Cincinnati, Ohio as "DRI-WEAVE."

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer through the topsheet faster than if the body surface was not hydrophilic. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al. Alternatively, the body surface of the topsheet can be made hydrophilic by treating it with a surfactant such as is described in the above referenced U.S. Pat. No. 4,950,254.

Backsheet

The backsheet prevents the exudates absorbed and contained in the absorbent core from wetting articles that contact the sanitary napkin such as pants, pajamas and undergarments. The backsheet (3) is impervious to liquids (e.g., menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapors to escape from the absorbent structure (i.e., be breathable) while still preventing exudates from passing through the backsheet.

Permeation Blockage Means

Figure 2:
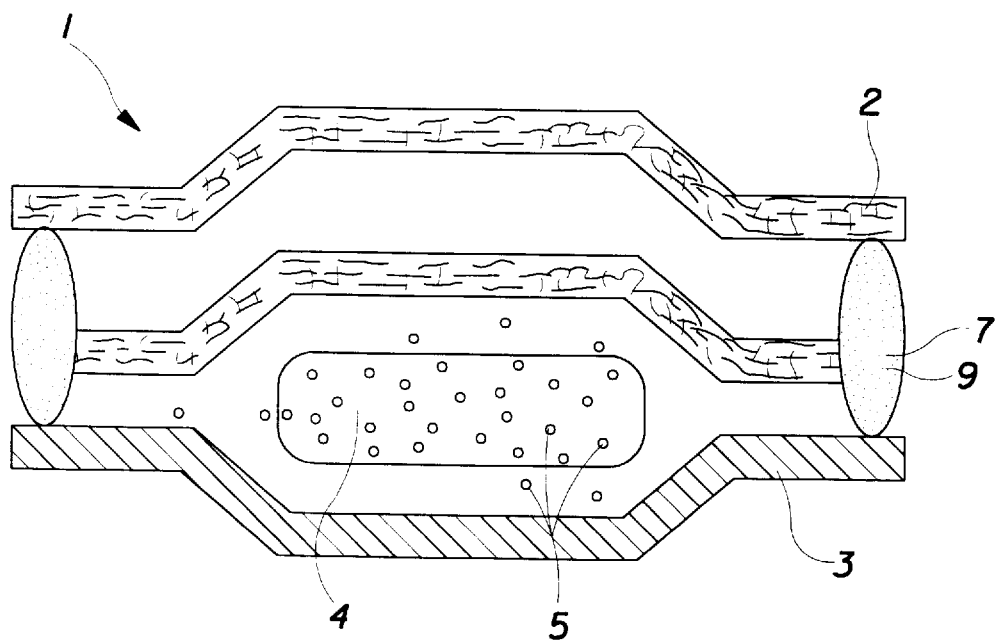
FIG. 2 in a cross sectional view of an embodiment according to the present invention where a particle migration shield is inserted between the topsheet and the absorbent structure containing particles.
Figure 3:
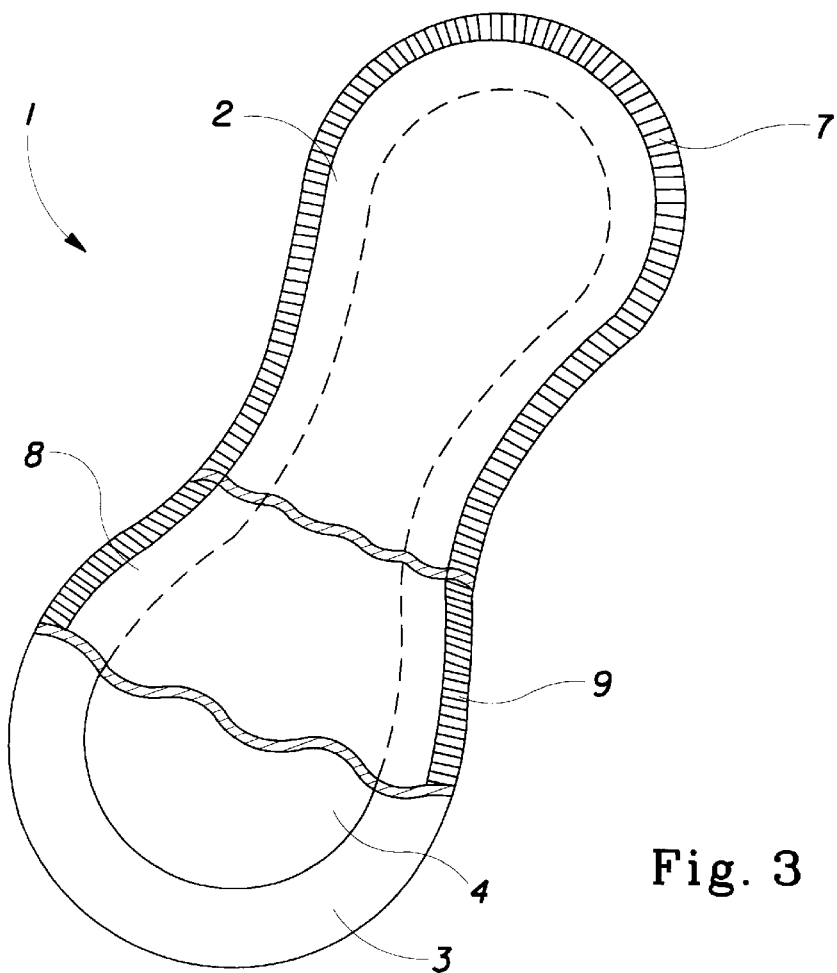
FIG. 3 is a partially cut away top plan view of the embodiment of FIG. 2.
Figure 4:
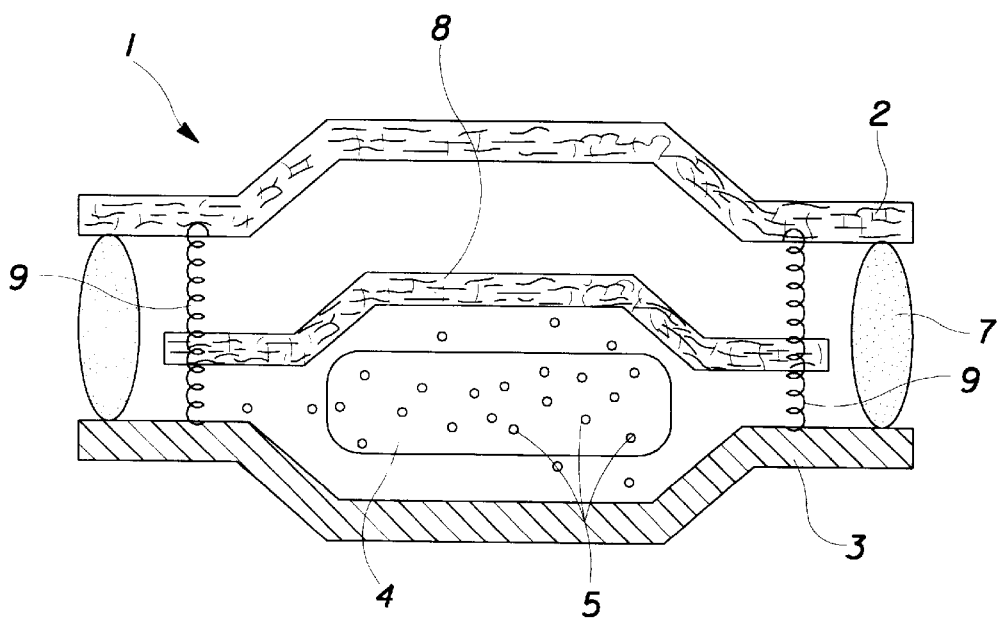
FIG. 4 is an alternative embodiment of FIG. 2.

The purpose of the permeation blockage means is to positively shield all particles from possible migration out of the absorbent product. The permeation blockage means (8) as shown in FIG. 2, 3 and 4 is a structural part of the absorbent product according to the invention. As such it can be considered part of the topsheet which then could be called a multi-layer topsheet or composite topsheet. It also could be considered part of the core, for example as the primary or optional distribution layers.

The permeation blockage means can be made of a variety of materials as long as its main function is satisfied. The materials for the permeation blockage means can be woven or non-woven materials or even films. Naturally, since the permeation blockage means is interim the topsheet (2) and the absorbent core (4), a liquid communication through it must be possible, at least in the direction from the topsheet towards the absorbent core.

Preferred material for the permeation blockage means is a non-woven tissue made of natural or synthetic fibres like those mentioned when describing the absorbent core above. Particularly preferred are tissues of natural fibres such as cellulose, or modified natural fibres such as cross-linked cellulosic materials. It should also be mentioned that for permeation blockage means having the same periphery as the topsheet or the backsheet it is advantageous that their fluid communication capability does not lead to undesired wicking of fluids within the absorbent product towards the peripheral edge of the product. Therefore, permeation blockage means are desired which have directional wicking such that peripheral leakage induced by wicking within the permeation blockage means is prevented.

In order to assess whether an absorbent product is susceptible to the present invention it first has to be assessed whether particles could migrate to the liquid passage ways. For example a sanitary napkin can comprise an absorbent core consisting entirely of a fluid storage layer which is provided as a laminate. The laminate encloses particulate absorbent gelling material as indicated above. It now has to be reviewed whether absorbent gelling material particles could migrate from the laminate to the liquid passage ways in the topsheet. If the laminate for example is cut at its longitudinal or lateral edges particles can escape there. If, however, the laminate is formed such that it fully encloses the absorbent gelling material particles, these particles would not benefit from a permeation blockage means and the product would not be susceptible to the present invention.

An endless seal (9) has to limit the possible migration paths of the particles from the liquid passage ways in the topsheet. If there is only a limited area in which liquid passage ways are present in the topsheet, this can be accomplished by joining the permeation blockage means only to the topsheet. It also is possible to join the permeation blockage means only to the backsheet outside the periphery of the core but inside the periphery of the backsheet. However, it is preferred to seal the permeation blockage means to the topsheet as well as to the backsheet, and preferably, indicated as number 7, 9 in FIG. 2 and 3. along a common endless peripheral edge.

This joining of the permeation blockage means to the absorbent product can be accomplished by adhesive, by welding or as indicated in FIG. 3 by crimping. In general the same means which are common for joining the compounds of the absorbent product together can be used for the permeation blockage means.

The permeation blockage means preferably is used in absorbent products comprising absorbent gelling materials in particulate form. For example, the particle size distribution of commercially available particles, designated Shokubai L74, of the Shokubai Company, Tokyo, Japan, has 90% particles greater than 160 micro meters. In other samples even less than 1% of particles have been found to be smaller than 45 micro meters. Particle size is measured by a sieve test series well known in the art end e.g. disclosed in European Application EP-A-0 576 738. It has been found to be satisfactory for the permeation blockage means if particles of the size of about 60 micro meters and less, and even more so for the size of about 45 micro meters and less, can still migrate through the permeation blockage means. This is believed to be so because they are neither contributing substantially to the absorbent capacity of absorbent products and are also not necessarily noticed by users of absorbent products. Therefore, permeation blockage means having a maximum pore size smaller than 60 micro meters, preferably smaller than 45 micro meters, are especially useful in embodiments of the present invention.

Optional components of the absorbent products

Optionally, the absorbent product of the present invention can comprise all those components typical for the particularly intended product use. For example catamenials, panty liners and sanitary napkins often comprise components such as wings and panty fastening adhesives in order to improve their positioning and soiling protection performance. Baby diapers comprise adhesive or mechanical closure systems such as tapes and dedicated fastening surfaces or velcro (TM) systems. Elasticated waistbands, waistbelts and other waist features are also common in baby diapers or adult incontinence products. Leg elastication by one or several elastic strands is also common in the art of absorbent products. In general, all typically used components in absorbent products can also be comprised in the absorbent products according to the present invention as long as a particle blockage means is present.

What is claimed is:

1. An absorbent product comprising a topsheet having liquid passage ways, a liquid impervious backsheet, and an absorbent core interposed between said topsheet and said backsheet; said core comprising dry particles, said particles being capable of permeating in their dry state through said topsheet along said liquid passage ways; said topsheet having a central region which comprises said liquid passage ways and an external region which is impermeable to said particles; said absorbent product further comprising a permeation blockage means to restrict permeation of said particles to said liquid passage ways; said permeation blockage means being between said core and said topsheet; said permeation blockage means being joined to either or both of said topsheet and said backsheet of said absorbent product in order to shield either said particles from said liquid passage ways or said liquid passage ways from said particles; said permeation blockage means extending beyond the periphery of said central region.

* * * * *